United States Patent [19]

DeGregorio et al.

[11] Patent Number: 5,605,700
[45] Date of Patent: Feb. 25, 1997

[54] TOPICAL ADMINISTRATION OF TOREMIFENE AND ITS METABOLITES

[75] Inventors: Michael W. DeGregorio, Granite Bay, Calif.; Kauko O. A. Kurkela, Espoo, Finland

[73] Assignee: Orion-Yhtyma Oy, Espoo, Finland

[21] Appl. No.: 313,103

[22] PCT Filed: Mar. 25, 1993

[86] PCT No.: PCT/FI93/00119

§ 371 Date: Oct. 31, 1994

§ 102(e) Date: Oct. 31, 1994

[87] PCT Pub. No.: WO93/19746

PCT Pub. Date: Oct. 14, 1993

[30] Foreign Application Priority Data

Apr. 3, 1992 [GB] United Kingdom ............... 9207437

[51] Int. Cl.$^6$ .................................................. A61F 13/00
[52] U.S. Cl. .................. 424/448; 424/449; 514/648; 514/937; 514/944; 514/969
[58] Field of Search ........................... 424/448, 449; 514/648, 944, 937, 969

[56] References Cited

U.S. PATENT DOCUMENTS

| | | | |
|---|---|---|---|
| 4,919,937 | 4/1990 | Mauvais-Jarvis et al. | 424/449 |
| 4,990,538 | 2/1991 | Harris et al. | 514/648 |
| 4,996,225 | 2/1991 | Toivola et al. | 514/428 |
| 5,132,115 | 7/1992 | Wolter | 424/448 |
| 5,189,212 | 2/1993 | Ruenitz | 562/468 |

FOREIGN PATENT DOCUMENTS

| | | |
|---|---|---|
| 0985875 | 12/1983 | European Pat. Off. . |
| 0240131 | 10/1987 | European Pat. Off. . |

OTHER PUBLICATIONS

"Cyclodextrins in the Pharmaceutical Field", O. Bekers et al., Drug Development and Industrial Pharmacy, 17(11), pp. 1503–1549 (1991).

Primary Examiner—D. Gabrielle Phelan
Attorney, Agent, or Firm—Burns, Doane, Swecker & Mathis

[57] ABSTRACT

Transdermal preparations containing as active ingredient toremifene or one of its metabolites N-demethyltoremifene or 4-hydroxy-toremifene or their pharmaceutically acceptable non-toxic salts are useful for the treatment of cancers localized in the skin or on a short distance form the skin such as metastatic lesions of breast cancer. They may also be used in adjuvant therapy of breast cancer and in the reversal of multidrug resistance of cancer cells to cytotoxic drugs. Such transdernal preparations are of particular interest in the treatment of melanoma, lymphoma, Kaposi's sarcoma and fungoides mycosis.

21 Claims, 3 Drawing Sheets

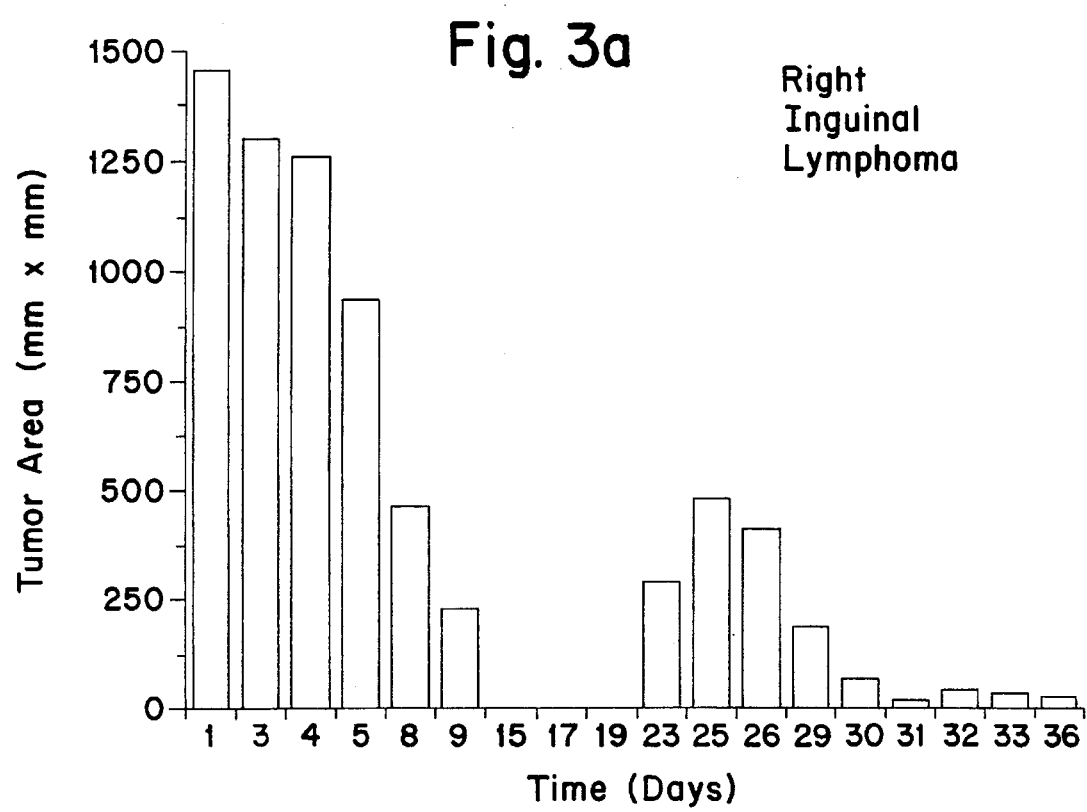
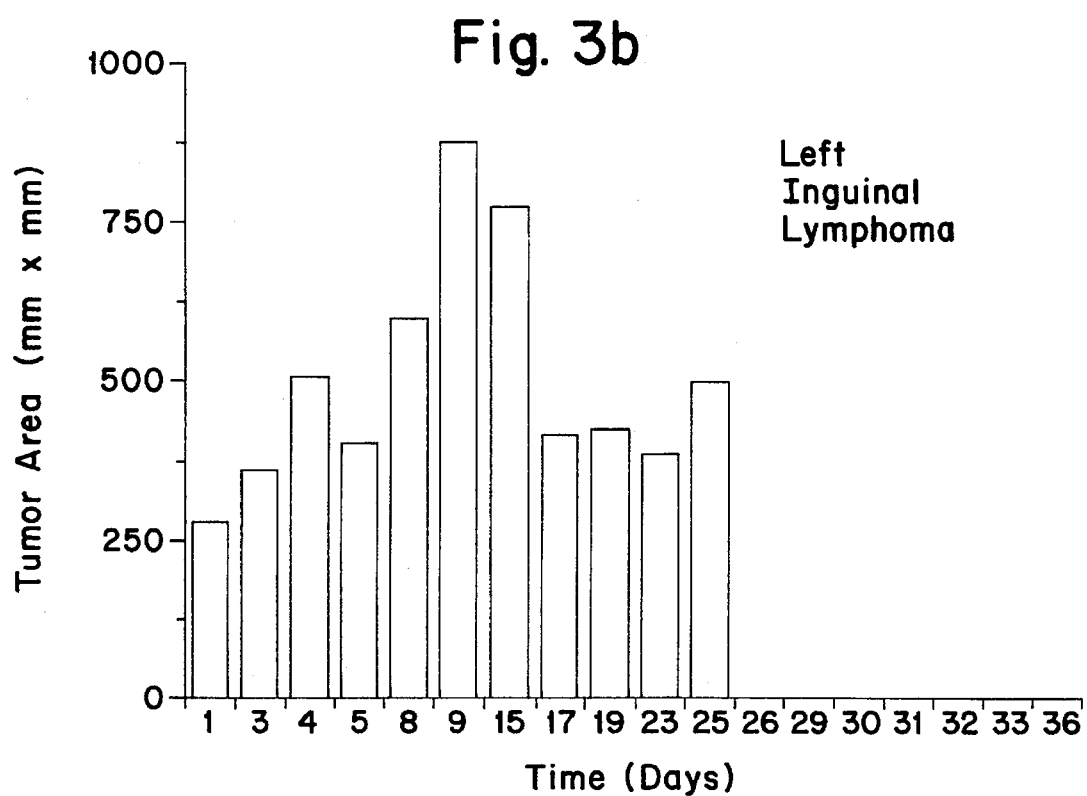

TOPICAL ADMINISTRATION OF TOREMIFENE AND ITS METABOLITES

This invention relates to topical preparations containing as active ingredient toremifene or one of its metabolites N-demethyltoremifene (4-chloro-1,2-diphenyl-[4-[2-(N-methylamino)ethoxy-]phenyl]-1-butene) or 4-hydroxytoremifene (4-chloro-1-(4-hydroxyphenyl)-2-phenyl-1-[4-[2-(N, N-dimethylamino)ethoyoxy]phenyl]-1-butene) or their pharmaceutically acceptable non-toxic salts. The use of such topical preparations e.g. for the treatment of cancers localized in the skin or on a short distance from the skin such as metastatic lesions of breast cancer is also within the scope of the invention. Moreover, the use of these topical preparations for the adjuvant therapy of breast cancer as well as their use for the reversal of multidrug resistance of cancer cells to cytotoxic drugs are also within the scope of the invention. Topical administration of toremifene or its metabolites are of particular interest in the treatment of melanoma, lymphoma, Kaposi's sarcoma and fungoides mycosis.

Tamoxifen and toremifene are triphenylethylene antiestrogens used in the treatment of estrogen receptor positive breast cancer. These drugs are the most frequently prescribed as endocrine agent for the treatment of breast cancer. Tamoxifen and toremifene inhibit estrogen-induced growth by competitive antagonism of tumor estrogen receptors (ER's). Antiestrogen therapy is effective in prolonging a disease-free state and overall survival of women following primary surgery. Antiestrogen therapy delays recurrence and prolongs survival in patients with primary breast cancer undergoing adjuvant therapy after mastectomy. About two-thirds of patients with estrogen receptor (ER) positive metastatic breast cancer will have a temporary remission on tamoxifen. Although tamoxifen is considered a relatively benign drug, recent evidence suggests that women receiving tamoxifen as adjuvant therapy may have increased risk of developing endometrial neoplasms (Fornander T et al, Lancet 1989, 21:117–120). Histopathology identifies these tumors as infiltrating endometrial tumors unrelated to breast tumor metastasis. The factors contributing to this increased risk are not well understood. However, a variety of studies have linked endometrial cancer to agents with estrogen activity (Smith Dc et al, N England J Med 1975; 293: 1164–67).

The development of multidrug resistance (MDR) is one of the major mechanisms by which cancer becomes refractory to chemotherapeutic agents, especially anthracyclines and the vinca alkaloids. Classical MDR is associated with the overexpression of a mdr-1 gene that codes for a plasma membrane P-glycoprotein (p170). The expression of the MDR-1 gene is believed to be associated with a decreased cellular accumulation of drug due to an active dependent efflux mechanism.

Although many agents including verapamil, the trifluoperizines, and cyclosporins have been shown to reverse multidrug resistance in vitro, most agents do not achieve high enough in vivo concentrations to reverse without substantial toxicity to the patient. This is particularly true for verapamil which is associated with significant cardiotoxicity.

The non-steroidal triphenylethylene antiestrogens have demonstrated in vitro chemosensitizing activity apparently unrelated to their antiestrogenic effects. Toremifene and its metabolites N-demethyltoremifene and 4-hydroxytoremifene are examples of new triphenylethylenes that have chemosensitizing activity in MDR-positive cells at concentrations that are achieved in humans without significant toxicity. Toremifene appears to be unique in that concentrations that reverse resistance in vitro (5 µM) can be achieved in vivo following oral therapy without substantial toxicity (Wiebe VJ et al, Cancer Chemother Pharmacol, 1990, 25: 247–251). Plasma concentrations of toremifene and N-demethyl-toremifene following large oral doses are on the order of 10 µM. However, plasma concentrations may not reflect the effective anti-MDR activity at the tumor level. Although the systemic toxicity of high-dose toremifene (400 mg/day) is generally confined to vertigo, nausea and hot flashes, combination therapy with other cytotoxic agents may alter the systemic toxicity profile.

Therefore, methods of increasing the tumor concentration of toremifene or its metabolites while minimizing systemic exposure may improve the efficacy of anti-MDR therapy with these drugs.

It has now been found that topical administration of toremifene and its metabolites can be used in order to achieve very high local tumor concentrations without the risk of systemic toxicities. Such topical preparations of toremifene and its metabolites are useful in the treatment of cancers localized in the skin or on a short distance from the skin, such as melanoma, lymphoma, Kaposi's sarcoma, fungoides mycosis and localized metastatic lesions of breast cancer. In addition, topical administration may lead to an effective method of preventing the recurrence of breast cancer in high-risk patients while minimizing the risk of endometrial tumors and systemic toxicity.

The transdermal administration of toremifene and its metabolites can be accomplished mainly in two different ways: (i) by mixing the therapeutically active compound or its non-toxic pharmaceutically acceptable salt with suitable pharmaceutical carriers and optionally penetration enhancers to form ointments, emulsions, lotions, solutions, creams, gels or the like, where preferably an amount of said preparation is applied onto a certain area of skin, or (ii) by incorporating the therapeutically active substance into patches or transdermal delivery systems according to known technology.

Examples of suitable excipients include those well known in the art of pharmacy for the preparation of topical formulations such as DMSO, vegetable and animal oils, non-volatile fatty alcohols, acids, esters, e.g. cetostearyl alcohol and cetyl alcohol; volatile alcoholic compounds, e.g. ethanol or isopropanol; glycols and glycol ethers, polyethylene glycol, polypropylene glycol, glycerol and glycerol ethers, cellulose derivatives, e.g. methylcellulose or carboxymethyl cellulose. Emulsifying agents, e.g. sorbitan stearate or polysorbate 60, and preserving agents and penetration enhancers known in the art may also be included.

The dissolution properties into aqueous media of toremifene and its metabolites can be significantly improved by complexation of the drug substance with cyclodextrins. Cyclodextrins (including alpha, beta and gamma cyclodextrins and their derivatives) are all cyclic oligomers of glucose. The cyclodextrins can form inclusion complexes with drugs in that drug molecule is included in the lipophile-seeking cavities of the cyclodextrin molecule. Therefore the cyclodextrins effectively solubilize lipophilic drugs into aqueous media. The use of cyclodextrins in the pharmaceutical field has been described e.g. in Drug Development and Industrial Pharmacy, 17(11), 1503–1549, 1991.

Dose range of toremifene or its metabolites for prevention/adjuvant therapy is in the order of 1–200 mg/day/person in humans depending on the bioavailability of the drug. The preferred dose would be close to adjuvant oral dose of 60 mg/day, or a single weekly dose of 300–500 mg/patch. For high-dose short course toremifene (or toremifene metabolite) a dose of 400–1000 mg/day is suggested; preferably 500–600 mg/day.

EXPERIMENTS

Following extensive studies were carried out to substantiate the present invention:

Experiment 1 describes tissue distribution of toremifene and its metabolites following short course high-dose topical vs. intraperitoneal (IP) administration in the mouse, as well as tissue distribution of antiestrogenic doses of toremifene and its metabolites following single dose topical vs, IP administration.

Experiment 2 describes efficacy of toremifene and its metabolites following topical administration in preventing breast cancer tumor growth in the mouse.

Experiment 3 describes efficacy of high-dose topically administered toremifene in enhancing doxorubicin cytotoxicity in MDR tumors in the mouse.

Experiment 4 describes efficacy of toremifene and its metabolites following topical adminstration in preventing lymphoma growth in the baboon.

Experiment 5 describes tissue distribution of toremifene following topical administration in Monodelphis domestica and the cytostatic effect of toremifene in melanoma cell lines.

BRIEF DESCRIPTION OF THE DRAWINGS

In the drawings,

FIG. 3a shows the response observed in baboon right inguinal lymphoma treated with topical toremifene, and FIG. 3b shows the response observed in the untreated baboon left lymphoma.

EXPERIMENT 1

Figure 1:
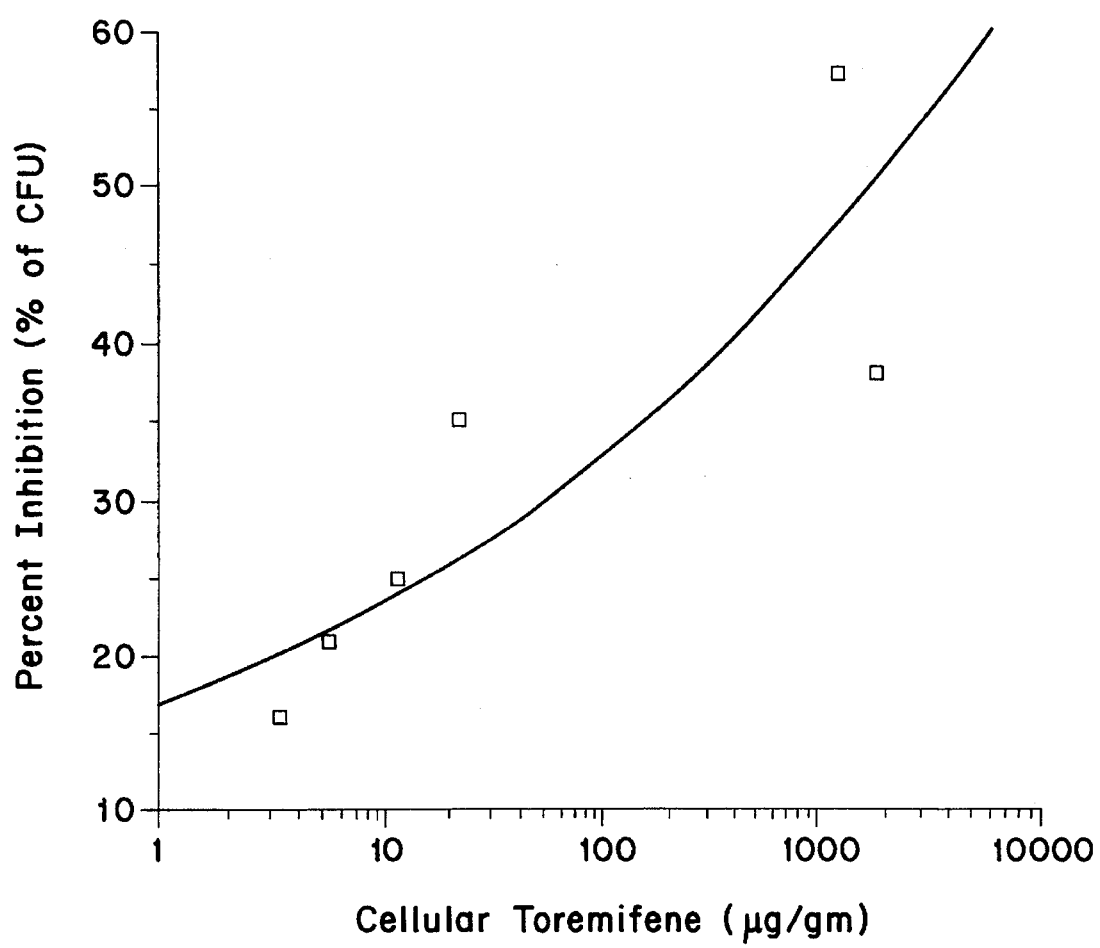
FIG. 1 shows the results of cloning studies performed on the tumors excised from mice treated with topical and intraperitoneal toremifene.

Methods:

Sixteen female athymic nude mice were injected with a 20-gauge needle subcutaneously with $5 \times 10^6$ MDA A-1 cells in the left scapular area. The tumors were allowed to grow for three weeks prior to treatment.

For IP administration toremifene citrate was suspended in peanut oil. Each of the three mice were injected IP using an 18 gauge needle with 50 µl, delivering 1 mg/day for five days. Topical toremifene was administered in a mixture of DMSO/ETOH/methylcellulose/water (10:25:7:58) at a dose of 2.5 mg/animal/day for 5 days. Toremifene citrate was first dissolved in DMSO and then diluted in the mixture of ETOH, methylcellulose and water. All mice were sacrificed on the fifth day of treatment two hours after the final dose. Blood specimens were collected by capillary pipette after disruption of axillary vessels and placed into heparinized centrifuge tubes. The brains, livers, and uterus were removed surgically and placed in separate tubes.

Single dose toremifene was administered by IP as described above, or topically with DMSO/ETOH/methylcellulose/water as the diluents. The dose of IP or topical toremifene was 500 µg. Tissue samples were collected as above.

All blood samples were centrifuged at 1,000 g. The plasma was collected, measured for volume, and placed in clean extraction tubes. All remaining tissue samples were weighed, placed in extraction tubes, and spiked with an internal standard, nafoxidine. The tissues were thoroughly homogenized before the addition of 6 ml extraction fluid. Samples were collected and dried as described below. Before injection onto the HPLC column, each sample was reconstituted with 200 µl methanol. All samples were placed in a quartz cuvette for UV activation. The brain samples required filtration with disposable syringe filters. Concentrations of toremifene was calculated for all samples based on the standard curve.

Toremifene and its metabolites were quantified by high performance liquid chromatography (HPLC).

Results

Table 1 shows that topically treated tumors had 150 times greater concentrations of toremifene while having a lower serum concentration at 2.5 times the dose of intraperitoneal administration. This indicated a clear pharmacologic advantage. Interestingly, the mice receiving topical toremifene had one-tenth the concentrations in the uterus compared to those receiving IP toremifene. In the liver, the topically treated mice also showed lower toremifene concentrations suggesting less systemic distribution. The toremifene concentrations in the brain tissue were equivalent. Table 2 shows that the topically treated tumors had a greater concentration of N-demethyltoremifene while having a lower serum concentration. This indicates that MDA A-1 tumor cells may metabolize toremifene. There was essentially no difference in concentration in the liver between the intraperitoneal and topically treated tumors. The brains and uteri of the topically treated mice also showed less N-demethyltoremifene concentration than the IP treated group.

Table 3 shows that the topically treated tumors had greater concentrations of trans 4-hydroxytoremifene than those treated IP. This metabolite is the most potent antiestrogenic metabolite. Serum levels in the topically treated tumors were lower, while in the brain, concentrations were identical.

We also examined the in vitro uptake of toremifene in the MCF-7 ER+cells at effective antiestrogenic drug doses and compared these studies with the results from the in vivo distribution studies described above. Following 20 hour incubation with 6.6 µM toremifene, cells were washed, counted, weighed and cellular toremifene concentrations were measured by HPLC. The concentration of toremifene (µg/mg) is shown in Table 4.

By comparison to toremifene concentrations achieved in tumors following topical and intraperitoneal routes of administration, the largest concentrations are seen following topical administration of toremifene. Topical administration resulted in greater than 7 times the toremifene concentration found after in vitro exposure and greater than 150 times that found following intraperitoneal injection. These results suggest that the concentrations of toremifene can easily be obtained following topical administration to subcutaneous tumors whereas intraperitoneal administration was 1/20 of the in vitro uptake data, thus suggesting a further kinetic advantage of topical therapy.

Table 5 shows the toremifene concentrations following a single dose of 500 µg IP vs 500 µg administered topically. DMSO and methylcellulose were used as the diluents. Both topically administered methods had similar tumor levels compared to IP but had much less systemic distribution. This was trend noted in both serum and uterus.

Discussion:

In the experiment, we demonstrate that toremifene readily undergoes transdermal penetration and achieves very high tumor concentrations while limiting systemic exposure. Interestingly, while more toremifene could be delivered topically to the tumors, the serum concentrations were much lower indicating a significant therapeutic advantage for topical delivery of toremifene. In addition, both the active N-demethyl- and 4-hydroxy-metabolites of toremifene were present in greater concentrations in tumor tissue following topical delivery than IP suggesting that metabolism to these active metabolites may also occur at the tissue level rather than exclusively in the liver.

The uterus and liver had much lower toremifene concentrations after topical delivery than IP providing further evidence of reduced systemic exposure with topical therapy. Reduced uterine exposure may be a significant clinical advantage due to the potential risk of secondary tumors to the antiestrogens. Following prolonged adjuvant treatment with tamoxifen, endometrial dysplasia, bleeding, polyp formation and tumors have been reported (Nuovo MA et al Int J Gyn Pathol 1989; 8: 125–131). Tamoxifen metabolites (Bisphenol and metabolite E) following tamoxifen therapy that are present in uterine tissue may potentially be associated with the development of secondary uterine neoplasms (Nuovo MA et al, Int J Gyn Pathol 1989; 21: 117–120). Topical administration of toremifene may circumvent the potential for these side effects.

EXPERIMENT 2

Methods:

In this study 12 mice were transplanted with MCF-7 cells and were allowed to grow until a small tumor was detected in all mice ($<1$ mm$^3$). At that time mice were divided into three groups of four mice each. One group received the diluent alone (DMSO, 20 µl) topically, the second group received 500 µg of 4-OH-toremifene by topical administration, and the third received 500 µg/day of toremifene by topical administration. All mice received the same amount of diluent/day (20 µl). The study was assessed following 15 days of treatment.

Results:

All four control mice had developed tumors ($>6\times8$ mms). In the other groups only one mouse in the 4-OH-toremifene group developed a small tumor ($<2\times1$ mms). This experiment clearly shows that topical administration of 4-OH-toremifene or toremifene prevented tumor growth.

Discussion:

This experiment clearly demonstrates that adjuvant doses of topically administered toremifene or its metabolites can prevent breast cancer tumor growth in an in vivo mouse model. This result coupled with the kinetic advantage of topical administration (Experiment 1) suggests that topical toremifene can achieve the desired antiestrogenic effects without systemic distribution.

EXPERIMENT 3

Methods:

The topical administration toremifene citrate was dissolved in 1.0 ml of dimethyl sulfoxide (DMSO) resulting in a solution delivering 2.5 mg toremifene/60 µl. Drug was applied dropwise to the skin surface directly and around the tumor. Each drop was allowed to evaporate completely. This treatment was administered once a day at the same time for a total of five days. All mice were sacrificed on the fifth day of treatment two hours after the final dose. Tumors were collected sterilely and processed for clonogenic assay.

Following toremifene administration tumors were excised and a portion of each tumor was extracted for HPLC analysis. The remaining portion was cloned following a 1 hour exposure to doxorubicin 1 µg/ml. The percent inhibition was determined after 14 days, and plotted against the toremifene concentration in each individual tumor.

Results:

FIG. 1 shows the results of cloning studies performed on the tumors excised from mice treated with topical and intraperitoneal toremifene. As shown in the graph there was a good correlation between percent inhibition and cellular toremifene concentration at 14 days (r=0.77). In addition, all three topically treated tumors achieved >30% inhibition, whereas all three intraperitoneal treated tumors had <30% inhibition.

Figure 2:
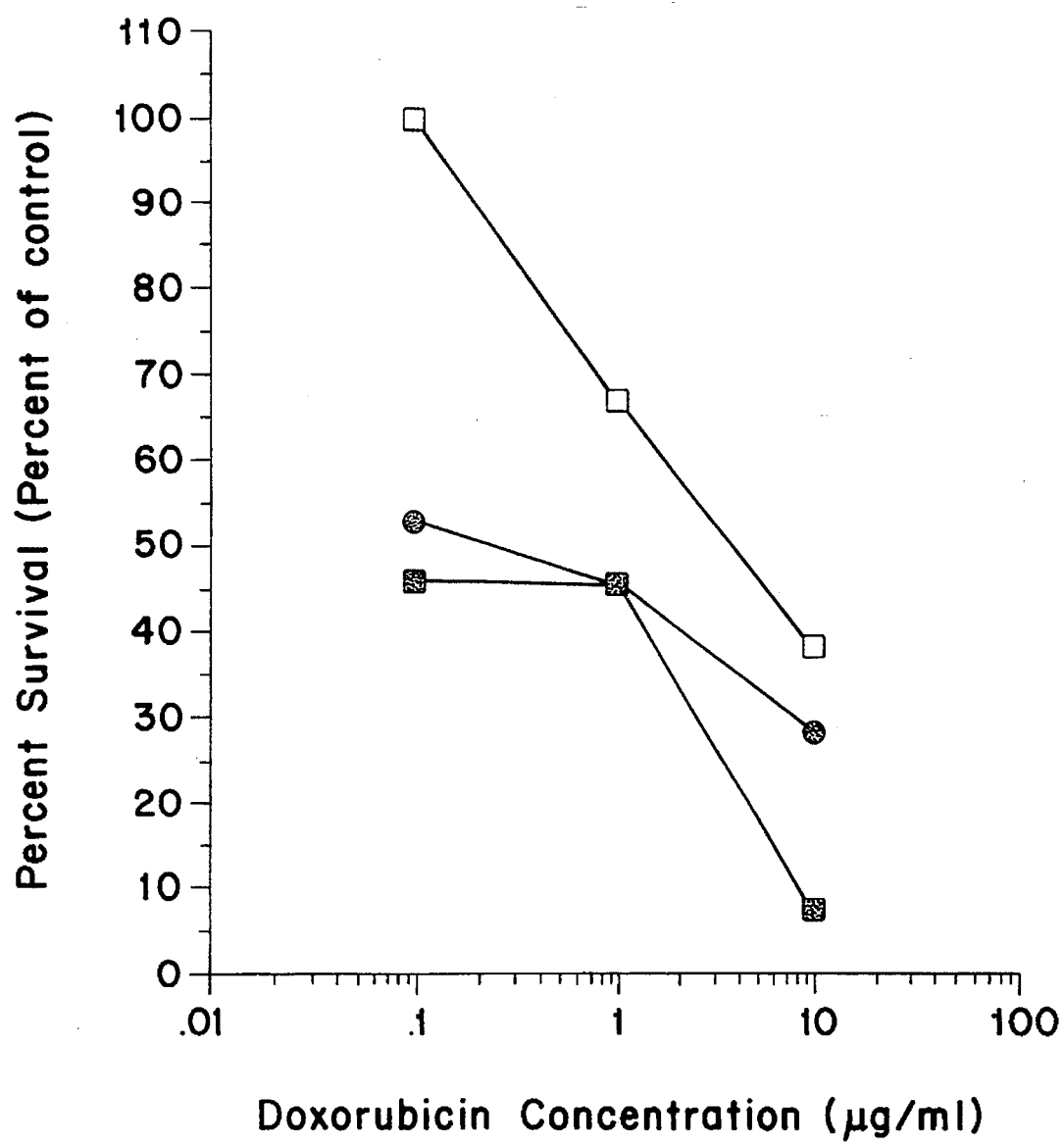
FIG. 2 shows the results of cloning studies performed on tumors excised from mice treated with and without topical toremifene.

FIG. 2 shows the results of cloning studies performed on tumors excised from mice treated with and without topical toremifene. The top curve show a tumor resistant to doxorubicin in a mouse not treated with toremifene. The bottom two curves show tumors that were treated with toremifene. Clearly, toremifene appears to sensitize these MDR MDA A-1 tumors to doxorubicin.

Discussion:

These results suggest that the high achievable tumor toremifene concentrations seen with topical toremifene in vivo, the greater the synergistic effects will be at reversing the acquired drug resistance to doxorubicin.

EXPERIMENT 4

Methods

Topical toremifene therapy of a 15-year old female baboon with a spontaneous non-Hodgkin's lymphoma was evaluated. Enlarged lymph nodes with diameters of 1–2 cm were evident in the both groins. Toremifene was dissolved in a. mixture of dimethylsulfoxide, ethanol and methylcellulose. Over a period of 8 days, a total of 1.4 g toremifene was applied primarily on the right tumor region. Following 15 days from the start of topical therapy, an oral treatment with 1 g of toremifene on days 15, 17, 19 and 23 was instituted, with a total dose of 4 g. On day 25 following start of treatment, topical therapy of right groin was re-instituted while continuing the oral treatment. During that period, a total of 1.4 g of toremifene was administered transdermally and 11 g orally. The response to therapy was determined by measuring the sizes of the tumors on two perpendicular dimensions.

Results

The response to the therapy is given in FIG. 3a and 3b. A clear response was observed in the treated right inguinal lymphoma whereas the untreated left lymphoma increased in size during the topical treatment period. During the oral toremifene therapy the left inguinal lymphoma stabilized, whereas the right inguinal lymphoma begun to regrow. Consequently, topical toremifene therapy was reinstituted on this tumor. Similarly to the initial response to topical therapy, the lymphoma regressed from tumor area of 476 mm$^2$ to 24 mm$^2$.

The treatment of a regional T-cell lymphoma in a female baboon showed that topical toremifene can produce an in vivo antitumor response.

EXPERIMENT 5

Methods

Toremifene in the form of toremifene citrate was first dissolved in DMSO, after which it was added to 3% methyl cellulose in ethanol to a final concentration of 1 mg/ml.

Six male *Monodelphis domestica* were given toremifene topically for 5 days. The dose was 0.5 mg/d in 3 and 1 mg/d in 3 animals. Toremifene was applied topically to shaved skin on a surface area of 1 cm² of the lower back. At day 5 the animals were sacrificed, and the concentrations of toremifene and its metabolites were measured in plasma, skin, testicles, liver, eyes, brains and heart.

Three human melanoma cell lines (TD 36, TD 30A and SK-MEL-31) and three experimental cell lines (TD 1.4, TD 7.2 and TD 8) derived from UVB-induced melanocytic nevi in *Monodelphis domestica* were grown in vitro to assess the cytostatic IC-50 values for toremifene. The metastatic melanoma cell line, SK-MEL-31, was obtained from the American Type Culture Collection (Rockville, Md.). Two additional human cell lines were derived from portions of surgigally-excised large diameter, superficial spreading melanomas. TD 1.4 was developed from a benign melanoma, whereas TD 7.2 and TD 8 were derived from melanocytic hyperplasias. IC-50 values were determined from semi-log plots of percent cell survival vs. concentration of toremifene citrate.

Results

The mean plasma and tissue concentrations of toremifene in 6 animals following topical administration of 0.5 and 1 mg/day for 5 days are given in Table 6. Toremifene concentration in skin was more than 500-fold as compared to other tissues.

The 50% growth inhibitory concentrations (IC-50) of the human and experimental cell lines for toremifene is shown in Table 7. Growth inhibitory effect of toremifene was very similar in all six cell lines of melanocyte origin. The IC-50s had a range of 5.8–9.6μM.

Discussion

In the experiment we demonstrated that toremifene has a clear cytostatic effect on human and experimental melanomatous cell lines in vitro. Although a cytostatic effect was observed in all cell lines, the concentrations needed to produce this effect were relatively high. However, topical administration of toremifene produces skin concentrations that are far beyond these in vitro concentrations, suggesting that a clear cytostatic effect could be obtained on cutaneous melanoma in vivo.

TABLE 1

Toremifene concentrations following 5 days of IP vs. topical treatment with toremifene

| Tissue | IP | Topical | Topical/IP |
|---|---|---|---|
| Tumor (μg/g) | 7.08 (3.55–11.86) | 1087.34 (23.47–1924.77) | 153.58 |
| Serum (μg/ml) | 4.37 (0.1–12.79) | 1.00 (0.46–1.84) | 0.23 |
| Brain (μg/g) | 1.85 (1.17–2.20) | 1.45 (1.29–1.61) | 0.78 |
| Uterus (μg/g) | 29.97 (26.47–35.90) | 2.94 (2.33–3.53) | 0.10 |
| Liver (μg/g) | 14.25 (11.2–18.60) | 4.21 (3.46–5.62) | 0.30 |

TABLE 2

N-demethyltoremifene concentrations following IP vs. topical treatment

| Tissue | IP | Topical | Topical/IP |
|---|---|---|---|
| Tumor (μg/g) | 1.27 (0.88–1.74) | 8.43 (1.15–13.86) | 6.64 |
| Serum (μg/ml) | 0.18 (0.10–0.30) | 0.08 (0.06–0.09) | 0.44 |
| Brain (μg/g) | 0.49 (0.26–0.73) | 0.29 (0.0–0.49) | 0.59 |
| Uterus (μg/g) | 1.18 (1.02–1.51) | 0.56 (0.38–0.76) | 0.47 |
| Liver (μg/g) | 0.94 (0.92–0.98) | 0.92 (0.80–1.10) | 0.98 |

TABLE 3

Trans 4-hydroxytoremifene concentrations following IP vs. topical treatment

| Tissue | IP | Topical | Topical/IP |
|---|---|---|---|
| Tumor (μg/g) | 0.88 (0.64–1.06) | 2.33 (0.82–3.26) | 2.65 |
| Serum (μg/ml) | 0.16 (0.12–0.20) | 0.10 (0.04–0.17) | 0.63 |
| Brain (μg/g) | 0.35 0.22–0.43) | 0.35 (0.31–0.40) | 1.00 |
| Uterus (μg/g) | 0.83 (0.46–1.05) | 0.70 (0.50–0.80) | 0.84 |
| Liver (μg/g) | 0.60 (0.56–0.66) | 0.98 (0.51–1.43) | 1.63 |

TABLE 4

Comparison of cellular concentrations of toremifene following in vitro exposure, intraperitoneal injection and topical administration

| Sample | Route of Administration | Toremifene Conc. |
|---|---|---|
| In Vitro (Cell pellets) | Direct Application | 0.149 μg/mg |
| In Vivo (Tumor) | Intraperitoneal Injection | 0.007 μg/mg |
| In Vivo (Tumor) | Topical Administration | 1.087 μg/mg |

Concentrations are average of three determinations.

TABLE 5

Toremifene concentrations following a single dose IP vs. topical treatment toremifene (500 μg) in DMSO or methylcellulose

| Tissue | IP | DMSO | MC | DMSO/IP | MC/IP |
|---|---|---|---|---|---|
| Tumor (μg/g) | 2.57 (1.64–4.46) | 4.65 (3.41–6.96) | 1.80 (0.95–3.10) | 1.81 | 0.70 |
| Serum (μg/ml) | 0.09 (0.04–0.14) | 0.03 (0.004–0.04) | 0.02 (0.00–0.04) | 0.33 | 0.22 |
| Uterus (μg/g) | 23.60 (13.58–40.17) | 0.92 (0.66–1.35) | 1.10 (0.64–1.92) | 0.04 | 0.05 |

TABLE 6

The mean concentration of toremifene in plasma (nmol/ml) and various tissues (nmol/g) following topical toremifene administration of 0.5 and 1 mg/day for 5 days in 6 male *Monodelphi domestica*.

|  | 0.5 mg/day | 1 mg/day |
|---|---|---|
| Plasma | 0 | 0 |
| Skin | 1296.40 ± 1003.93 | 1237.35 ± 768.90 |
| Liver | 1.07 ± 0.69 | 3.60 ± 2.23 |
| Testicles | 1.52 ± 2.13 | 0.52 ± 0.05 |
| Brain | 0.82 ± 0.99 | 0.82 ± 0.62 |
| Eyes | 0 | 0.17 ± 0.05 |
| Heart | 0 | 0.21 ± 0.16 |

TABLE 7

IC-50 values of the human and experimental melanomatous cell lines for toremifene

|  | Cell line | IC-50 (µM) |
|---|---|---|
| Human | TD 36 | 5.8 |
|  | TD 30 A | 7.7 |
|  | SD-MEL-31 | 8.1 |
| Experimental | TD 8 | 7.7 |
|  | TD 1.4 | 9.3 |
|  | TD 7.2 | 9.6 |

We claim:

1. A transdermal preparation comprising as active ingredient toremifene or one of its metabolites N-demethyl-toremifene(4-chloro-1,2-diphenyl-[4-[2-(N-methylamino) ethoxy]phenyl]-1-butene) or 4-hydroxytoremifene(4-chloro-1-(4-hydroxyphenyl)-2-phenyl-1-[4-[2-(N, N-dimethylamino)ethoxy]phenyl]-1-butene) or a pharmaceutically acceptable non-toxic salt thereof, together with one or more pharmaceutically acceptable excipients.

2. A preparation according to claim 1 which is in the form of an ointment, emulsion, lotion, solution, gel or cream.

3. A preparation according to claim 1 where the preparation is a transdermal delivery patch system.

4. A preparation according to claim 2 where the active ingredient is in the form of a complex of a cyclodextrin.

5. A preparation according to claim 1 where the active ingredient is toremifene or a pharmaceutically acceptable salt thereof.

6. A transdermal preparation according to claiam 1 for use in the treatment of breast cancer.

7. A transdermal preparation according to claim 1 for use in the adjuvant therapy of breast cancer.

8. A transdermal preparation according to claim 1 for use in the reversal of multidrug resistance of cancer cells to cytotoxic drugs.

9. A transdermal preparation according to claim 1 for use in the treatment of melanoma, lymphoma, Kaposi's sarcoma or fungoides mycosis.

10. A method of treatment of breast cancer comprising administering transdermally to a subject in need of such treatment an effective amount of a transdermal preparation comprising as active incredient toremifene or one of its metabolites N-demethyl-toremifene(4-chloro-1,2-diphenyl-[4-[2-(N-methylamino)ethoxy]-phenyl]-1-butene) or 4-hydroxytoremifene(4-chloro-1-(4-hydroxyphenyl)-2-phenyl-1-[4-[2-(N,N-dimethylamino)ethoxy]-phenyl]-1-butene) or a pharmaceutically acceptable non-toxic salt thereof, together with one or more pharmaceutically acceptable excipients.

11. A method for reversing the multidrug resistance of cancer cells to a cytotoxic drug comprising administering transdermally a multidrug resistance reversal effective amount of toremifene or one of its metabolites N-demethyltoremifene(4-chloro-1,2-diphenyl-[4-[2-(N-methylamino) ethoxy]-phenyl]-1-butene) or 4-hydroxytoremifene(4-chloro-1-(4-hydroxyphenyl)-2-phenyl-1-[4-[2-(N,N-dimethylamino)-ethoxy]phenyl]-1-butene) or a pharmaceutically acceptable non-toxic salt thereof, together with one or more pharmaceutically acceptable excipients, to a subject in need of such treatment.

12. A method of treatment of melanoma, lymphoma, Kaposi's sarcoma or fungoides mycosis comprising administering transdermally to a subject in need of such treatment an effective amount of a transdermal preparation comprising as active incredient toremifene or one of its metabolites N-demethyltoremifene(4-chloro-1,2-diphenyl-[4-[2-(N-methylamino)ethoxy]-phenyl]-1-butene) or 4-hydroxy-toremifene(4-chloro-1-(4-hydroxyphenyl)-2-phenyl-1-[4-[2-(N,N-dimethyl-amino)ethoxy]phenyl]-1-butene) or a pharmaceutically acceptable non-toxic salt thereof, together with one or more pharmaceutically acceptable excipients.

13. A preparation according to claim 3 where the active ingredient is in the form of a complex of a cyclodextrin.

14. A preparation according to claim 2 where the active ingredient is toremifene or a pharmaceutically acceptable salt thereof.

15. A preparation according to claim 3 where the active ingredient is toremifene or a pharmaceutically acceptable salt thereof.

16. A preparation according to claim 4 where the active ingredient is toremifene or a pharmaceutically acceptable salt thereof.

17. A transdermal preparation according to claim 2 for use in the treatment of breast cancer.

18. A transdermal preparation according to claim 3 for use in the treatment of breast cancer.

19. A transdermal preparation according to claim 4 for use in the treatment of breast cancer.

20. A transdermal preparation according to claim 5 for use in the treatment of breast cancer.

21. A transdermal preparation according to claim 2 for use in the reversal of multidrug resistance of cancer cells to cytotoxic drugs.

* * * * *